United States Patent [19]
DeMichele et al.

[11] Patent Number: 5,962,712
[45] Date of Patent: Oct. 5, 1999

[54] STRUCTURED LIPID CONTAINING GAMMA-LINOLENIC OR DIHOMOGAMMA-LINOLENIC FATTY ACID RESIDUE, A MEDIUM CHAIN (C6-C12) FATTY ACID RESIDE AND A N-3 FATTY ACID RESIDUE

[75] Inventors: Stephen Joseph DeMichele, Dublin, Ohio; Michael Donald Karlstad, Knoxville, Tenn.; Bruce Ryan Bistrian, Ipswich; Edward Anthony Mascioli, Needham, both of Mass.

[73] Assignee: Abbott Laboratories, Abbott Park, Ill.

[21] Appl. No.: 08/839,086

[22] Filed: Apr. 23, 1997

Related U.S. Application Data

[62] Division of application No. 08/410,581, Mar. 30, 1995, Pat. No. 5,661,180, which is a continuation of application No. 08/004,828, Jan. 15, 1993, abandoned.

[51] Int. Cl.$^6$ .................................................... C07C 53/00
[52] U.S. Cl. .............................................................. 554/224
[58] Field of Search ............................................... 554/224

[56] References Cited

U.S. PATENT DOCUMENTS

| | | | |
|---|---|---|---|
| 4,302,447 | 11/1981 | Horrobin | 424/145 |
| 4,526,902 | 7/1985 | Rubin | 514/560 |
| 4,528,197 | 7/1985 | Blackburn | 514/552 |
| 4,607,052 | 8/1986 | Mendy et al. | 514/547 |
| 4,701,469 | 10/1987 | Mendy et al. | 514/547 |
| 4,752,618 | 6/1988 | Mascioli et al. | 514/549 |
| 4,753,963 | 6/1988 | Jandacek et al. | 514/552 |
| 4,758,592 | 7/1988 | Horrobin | 514/549 |
| 4,843,095 | 6/1989 | Rubin | 514/558 |
| 4,871,768 | 10/1989 | Bistrian | 514/547 |
| 4,888,326 | 12/1989 | Horrobin | 514/27 |
| 4,898,885 | 2/1990 | Horrobin | 514/560 |
| 4,906,664 | 3/1990 | Bristrian et al. | 514/552 |
| 4,931,468 | 6/1990 | Horrobin | 514/560 |
| 4,965,075 | 10/1990 | Horrobin et al. | 424/638 |
| 4,970,235 | 11/1990 | Traitler et al. | 514/558 |
| 5,043,328 | 8/1991 | Weithmann | 514/78 |
| 5,081,105 | 1/1992 | Bistrian | 514/2 |
| 5,196,198 | 3/1993 | Shaw et al. | 442/195.1 |
| 5,227,403 | 7/1993 | Seto et al. | 514/547 |

FOREIGN PATENT DOCUMENTS

| | | |
|---|---|---|
| 2000391 | 10/1988 | Canada . |
| 421867 | of 0000 | European Pat. Off. . |
| 871142972 | 9/1987 | European Pat. Off. . |
| 300844 | 6/1988 | European Pat. Off. . |
| 8901364 | 3/1989 | WIPO . |
| 8900237 | 10/1989 | WIPO . |
| 8900239 | 10/1989 | WIPO . |
| WO 90/04012 | 10/1989 | WIPO . |

OTHER PUBLICATIONS

Hirschberg, et al., "The Response to Endotoxin in Guinea Pigs After Intravenous Blackcurrant Seed Oil," Lipids, vol. 25, 491–495, 1990.

Karlstad, et al., "Dietary Manipulation of Plasma Fatty Acid Profiles with γ–Linolenic Acid Enriched Parenteral Nutrition in Injured Rats," J. Parenteral Enteral Nutrition, vol., 16. 25S, 1992, No. S1A.

*Primary Examiner*—Samuel Barts
*Attorney, Agent, or Firm*—J. Michael Dixon; Thomas D. Brainard

[57] ABSTRACT

There is disclosed structured lipid containing either a gamma-linolenic acid or a dihomogamma-linolenic acid residue, together with an n-3 fatty acid residue and a medium chain fatty acid residue on the same glycerol backbone. This structured lipid is particularly well adapted to the treatment of disease or stress states. The gamma-linolenic or dihomogamma-linolenic acid residues modify the prostanoid synthesis pathway, reducing the level of series "2" prostanoids and elevating the levels of series "1" and "3" prostanoids. The n-3 fatty acid residue enhances the level of series "1" prostanoids as well as increases the production of series "3" prostanoids. The medium chain fatty acid residues enhances the absorption of the structured lipid. There is also disclosed enteral and parenteral diets as well as nutritional supplements containing the structured lipids of the invention.

20 Claims, No Drawings

STRUCTURED LIPID CONTAINING GAMMA-LINOLENIC OR DIHOMOGAMMA-LINOLENIC FATTY ACID RESIDUE, A MEDIUM CHAIN (C6-C12) FATTY ACID RESIDE AND A N-3 FATTY ACID RESIDUE

This application is a division of application Ser. No. 08/410,581, filed Mar. 30, 1995, now U.S. Pat. No. 5,661,180, which is a continuation of application Ser. No. 08/004,828 filed Jan. 15, 1993, abandoned.

TECHNICAL FIELD

The present invention relates to a new structured lipid and a method of treatment using the structured lipid. The structured lipid and method of the invention provide benefits in the treatment of a variety of disease and stress states. The structured lipid of this invention consists of a glycerol backbone with at least one gamma linolenic acid (18:3n-6 or GLA) or dihomogamma-linolenic acid (20:3n-6 or DHGLA) residue in combination with a medium chain ($C_6$–$C_{12}$) fatty acid residue and a $C_{18}$–$C_{22}$ n-3 fatty acid residue selected from alpha-linolenic (18:3n-3), and stearodonic (18:4n-3), eicosapentaenoic (20:5n-3) and docosahexaenoic (22:6n-3) acid. This structured lipid provides excellent nutritional support, is easily absorbed, and due to the unique proportions of n-3 and n-6 fatty acids will modulate the severity of eicosanoid-mediated diseases by reducing the level of potentially dangerous series "2" prostaglandins and series "4" leukotrienes in patients.

BACKGROUND ART

The term "lipid" generally denotes a heterogeneous group of substances, associated with living systems, which have the common property of insolubility in water but solubility in non-polar solvents such as hydrocarbons or alcohols. Included in the group are the oils and fats of our diet together with the so-called phospholipids associated with cell membranes. These substances have in common that they are esters of long-chain fatty acids.

Monocarboxylic, aliphatic fatty acids are the structural components common to most of the lipids that interest food chemists, and many of the properties of food lipids can be accounted for directly in terms of their component fatty acids. Almost without exception the fatty acids that occur in foodstuffs contain an even number of carbon atoms in an unbranched chain, e.g. lauric and dodecanoic acid. Besides the saturated fatty acids, of which lauric acid is an example, unsaturated fatty acids having one, two, or sometimes up to six double bonds are common.

Alpha-linolenic acid (systematically all-cis-9,12,15-octadecatrienoic acid) has the structure:

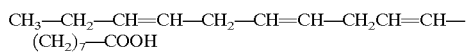

Gamma-linolenic acid is a less common isomer with double bonds at the 6-, 9- and 12-positions.

The system used for the identification of double-bond positions will be apparent by comparison of the structure with the systematic name. The structure of a fatty acid can be indicated by a convenient shorthand form giving the total number of carbon atoms followed by a colon and then the number of double bonds with the position of the double bonds given after the symbol Δ. Thus for example α-linolenic acid would be written simply as 18:3Δ9,12,15.

The oils and fats are obviously the lipids that most interest the food chemist. These consist largely of mixtures of triglycerides, i.e. esters of the trihydric alcohol glycerol (propane-1,2,3-triol), and three fatty-acid residues which may or may not be identical. "Simple" triglyceride molecules have three identical fatty-acid residues while "mixed" triglycerides have more than one species of fatty acid. Thus a naturally occurring fat will be a mixture of quite a large number of mixed and simple triglycerides. It is important to remember that organisms achieve a desirable pattern of physical properties for the lipids of, for example, their cell membranes or adipose tissue by utilizing an appropriate, and possibly unique, mixture of a number of different molecular species, rather than by utilizing a single molecular species which alone has the desired properties, as is the usual tactic with proteins and carbohydrates.

Fats and oils can be viewed in terms of their component triglycerides. The first descriptions of the glyceride structure of fats assumed that all their component triglycerides were simple. Thus a fat containing palmitic (hexadecanoic), stearic (octadecanoic), and oleic (cis-octadec-9-enoic) acids would be a mixture of the three triglyceride species tripalmitin, tristearin, and triolein. The first attempts to separate the component glycerides of fats, by the laborious process of fractional crystallization from acetone solutions at low temperatures, made it clear that much greater numbers of species of triglycerides occurred than would be expected from this simple concept. Fats and oils became recognized as clearly defined mixtures of mixed and simple triglycerides.

The fatty acids, in the form of the triglycerides of the dietary fats and oils, provide a major proportion of our energy requirements as well as, when in excess, contribute to the unwelcome burden of superfluous adipose tissue that so many of us carry. In recent years we have begun to appreciate that certain dietary fatty acids have a more particular function in human nutrition. Rats fed a totally fat-free diet show a wide range of acute symptoms affecting the skin, vascular system, reproductive organs, and lipid metabolism. Although no corresponding disease state has ever been recorded in a human patient, similar skin disorders have occurred in children subjected to a fat-free diet. The symptoms in rats could be eliminated by feeding linoleic or arachidonic acids (which in consequence became known for a time as vitamin F), and it is generally accepted that 2–10 g of linoleic acid per day will meet an adult human's requirements.

The identification of these two "essential fatty acids" in the 1930s preceded by some 25 years their identification as precursors of a group of animal hormones, the eicosanoids. Although animal tissues are unable to synthesize either of these two fatty acids, they readily convert the $C_{18}$ acid to the $C_{20}$ acid.

The many different eicosanoids all have similar structures. The reasons for the stringent requirements for the positions of the double bonds in essential fatty acids are clearly evident from the biosynthesis of prostaglandin $E_2$ from linoleic acid.

Other eicosanoids vary in the degree of reduction of the ring oxygens and presence of double bonds in the chain. Details of their numerous physiological activities are still accumulating in the scientific literature, but they are best known for their involvement in inflammation and the contraction of smooth muscle.

There are indications from studies of Eskimos that it is the high levels in their diets of certain polyunsaturated fatty acids (n-3 fatty acids which are abundant in fish oils) that are responsible for the remarkably low incidence of arterial disease in a population that appears to break all the usual nutritional rules. Fish oils are rich in fatty acids such as eicosapentaenoic acid (20:5Δ all cis-5,8,11,14,17) and docosahexaenoic acid (22:6Δ all cis-4,7,10,13,16,19). As seen from their structural formulae, these fatty acids are characterized by having a double bond in the n-3-position, i.e. at the third carbon atom when counting from the methyl end of the hydrocarbon chain. The nomenclature of n-3 is equivalent to the old ω-3 designation. This means that a quite distinct set of eicosanoids are derived from them compared with those from the so-called n-6-series. Prostaglandins synthesized from n-6 fatty acids are generally more active than those from n-3-fatty acids in promoting the formation of the blood clots that are involved in thrombosis. It remains to be seen whether these observations will lead to useful modifications of our diet or to changes in clinical practice.

For many years, it has been known that levels of thromboxane $A_2$, prostacyclin and $PGE_2$ (collectively "series 2 prostanoids") are elevated in endotoxemia and play a crucial role in septic and endotoxic shock, particularly in endotoxic shock caused by lipopolysaccharides from gram-negative bacteria such as *E. coli*. These same metabolites (series 2 prostanoids) have been shown to increase in a variety of other disease and stress states. Moreover, there is an imbalance between series-1 and series-2 prostaglandins in disease states such that the harmful series-2 prostaglandins predominate. Series 2 prostaglandins are formed from arachidonic acid (20:4n-6) which is derived from the n-6 fatty acid linoleic acid (18:2n-6) by enzymatic desaturation and elongation reactions.

Leukotriene $B_4$ ($LTB_4$) is a metabolite of arachidonic acid formed via a lipooxygenase enzyme. $LTB_4$ is a potent chemotactic agent for neutrophils and has been shown to stimulate neutrophils to secrete large quantities of potentially injurious mediators in inflammatory diseases. The use of n-3 fatty acids will regulate the intensity of n-6 prostaglandins and leukotriene biosynthesis since excess eicosanoid production can cause pathophysiology.

In the last few years, there have been a number of attempts to alter the relative supply of dietary n-3/n-6 fatty acids to modify the eicosanoid synthesis pathway and shift the proportions of series 1, series 2 and series 3 eicosanoids to produce a more desirable health status. It is known that both n-3 and n-6 types of fatty acids can be metabolically elongated and desaturated, however, the body cannot change the position of the double bonds; therefore, n-3 fatty acids cannot be converted to n-6 fatty acids and visa versa. Since each type of eicosanoid comes from a different family of fatty acids (e.g., n-3, n-6, n-9), diet modification is a promising course to modulate tissue eicosanoid biosynthesis.

U.S. Pat. No. 4,752,618 ("'618 Patent"), issued Jun. 21, 1988, the disclosure which is incorporated herein by reference, was one of the earliest references which discloses diet modification for treatment of disease. The '618 Patent describes the treatment of infection in patients through reducing the amount of n-6 fatty acids in the diet (particularly reduction of linoleic acid) by replacing a portion of the n-6 fatty acids with n-3 fatty acids. The optimum source of n-3 fatty acids disclosed in the '618 Patent is fish oil, e.g., menhaden oil. This dietary modification leads to the production of a larger proportion of series "3" prostanoids in place of series "2" prostanoids than normally is obtained from standard diets. Although the series "3" prostanoids, and the attendant reduction of series "2" prostanoids, has substantial beneficial effects, in some circumstances, particularly in the treatment of endotoxic shock, replacement of series "2" prostanoids with series "1" rather than the series "3" prostanoids might be even more beneficial. Series "1" prostanoids have already been shown to provide a certain amount of protection in endotoxic lung injury and traumatic shock.

The synthesis path for forming the series "1" prostanoids is from linoleic acid (18:2n6) to gamma-linolenic acid (18:3n6 or GLA) to dihomogamma-linolenic acid (20:3n6) to the series "1" prostanoids.

The following represents the metabolic pathway of linoleic acid to series "1" and "2" prostaglandins.

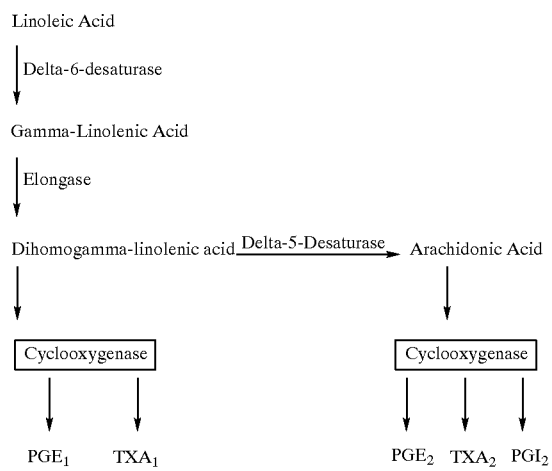

Dihomogamma-linolenic acid competes with arachidonic acid (20:4n6), for the enzyme cyclooxygenase. Cyclooxygenase is a critical enzyme in the formation of both the series "1" and series "2" prostanoids. When GLA is formed endogenously substantially all the gamma-linolenic acid is made into arachidonic acid, the precursor of the series "2" prostanoids. Accordingly, one could modify the diet to contain relatively high levels of gamma-linolenic acid in order to skew the prostanoid synthesis pathway to preferentially increase the production of series "1" prostanoids.

In a paper by Hirschberg et al., "The Response to Endotoxin in Guinea Pigs After Intravenous Blackcurrant Seed Oil," Lipids 25, 491–496 (1990) it is disclosed that high levels of blackcurrant seed oil, an oil rich in gamma-linolenic acid, was supplied as part of a parenteral diet to guinea pigs, who were then challenged with endotoxin. The results were somewhat disheartening; the gamma-linolenic acid provided no better protection (and possible worse systemic results) against endotoxin shock than did the classic lipid diet with soybean oil, a diet high in linoleic acid.

However, a recent study by Karlstad et al. JPEN 1992; 16(1):215 disclosed the measurement of the levels of dihomogamma-linolenic acid in the blood after the addition of 0, 2.7%, 4.4% and 6.1% gamma-linolenic acid to a parenteral diet. The authors found that for 4.4% and 6.1% gamma-linolenic acid enrichment, there was a 4–5 fold increase in the plasma dihomogamma-linolenic/arachidonate ratio. The increase in plasma dihomogamma-linolenic acid should lead to the production of more series "1" prostanoids.

The results of the Karlstad et al. and Hirschberg studies can be interpreted to mean that, beyond a certain level, dietary gamma-linolenic acid is not utilized properly. It may be that excess gamma-linolenic acid may be formed into arachidonic acid, leading to series "2" prostanoid buildup. Accordingly, one problem is how to achieve a higher level of dihomogamma-linolenic acid in plasma and tissues without parallel buildup of arachidonic acid.

It has been theorized that a structured lipid containing a medium chain fatty ($C_6$–$C_{12}$) acid residue may provide improved absorption of other fatty acids attached to the structured lipid. A recent paper by Jensen A.J.C.N. Suppl. no. 62; 1992 disclosed that a structured lipid containing medium chain fatty acid residues and long chain fatty acid residues (n-3 fatty acids from fish oil) are absorbed faster by the body than the physical mixture of the same fatty acids. There is no suggestion or teaching that a specific structured lipid would be useful to modify the prostanoid synthesis pathway.

U.S. Pat. No. 4,906,664 discloses a method of treating patients with cancer through administering a diet containing a structured lipid of the formula:

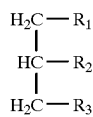

where one of $R_1$, $R_2$ and $R_3$ is a medium-chain fatty acid, and a second one of $R_1$, $R_2$ and $R_3$ is an ω fatty acid, and the third one of $R_1$, $R_2$ and $R_3$ is selected from the group consisting of hydrogen, hydroxyl, short, medium and long-chain fatty acids. This reference does not suggest or disclose the specific structured lipid of the instant application.

European Patent Application Number 87114297.2 discloses a triglyceride having a $C_8$ to $C_{14}$ fatty acid residue at the 2-position of the triglyceride and a residue of $C_{18}$ or higher fatty acids at the 1 and 3 position thereof. There is no suggestion or disclosure of the specific structured lipids of the instant invention nor the benefits that can be realized by feeding the structured lipids of this invention.

International Application No. PCT/DK 89/00239 filed Oct. 10, 1989 discloses the triglycerides 2-[docosahexaenoyl]-1,3-di(octanoyl/decanoyl) glycerol for nutritional compositions for enteral or parenteral purposes, especially as breast milk replacers.

International Application No. PCT/DK 89/00237 filed Oct. 10, 1989 discloses the triglycerides 2-arachidoyl-1,3-di(octanoyl/deconoyl) glycerol and the use of these materials in nutritional products.

International Application Number PCT/US89/01364 with a publication number of WO 89/09596 discloses a transesterification product of a mixture of fatty acids and triglycerides which include dairy fat as a primary component. A method of nutritional support using this composition is also disclosed.

International Application Number EP 421,867 discloses the production of structured lipids enriched in gamma-linolenic and/or stearidonic fatty acids. The process comprises hydrolysing a mixture of glycerides or the fatty material containing them with a lipase having specificity such as not to hydrolyse the ester bond of the gamma-linolenic and stearidonic fatty acids esterified in position 1, 2 or 3 and recovering the non-hydrolysed residue from the enzymatic reaction by separating the fatty acids produced.

Canadian Patent Application 2000391 with a WPI Accession Number of 90-139962/19 discloses the triglyceride 2-(alpha-linolenoyl)/gamma-linolenoyl)-1,3-di (octanoyol/decanoyl) glycerol as useful in nutritional compositions. It is suggested that these triglycerides are useful as components in nutritional compositions. The fatty acids are essential for control of tonus of smooth-muscle cells in the blood vessels or the tonus of the smooth muscle cells in the lungs and thus are useful in the control of respiratory distress. This reference does not suggest or disclose the specific structured lipids of this invention nor the methods of using them.

U.S. Pat. No. 4,528,197 discloses a method of enhancing protein anabolism in a hypercatabolic mammal, the method comprising parenterally administering an emulsion of triglycerides which, on hydrolysis, yields both long chain fatty acids and medium chain fatty acids.

U.S. Pat. No. 4,871,768 discloses a synthetic triglyceride comprising a glycerol backbone having three fatty acids attached thereto, said fatty acids being selected from a first group consisting of ω-3 fatty acids, and a second group consisting of caprylic acid, capric acid and mixtures thereof. This patent also discloses a method for minimizing the effects of infection and minimizing the effects of subsequent infection by administering a diet containing 10 to 80% by weight of an oily fraction, said oily fraction being the aforementioned fatty acid.

U.S. Pat. No. 4,701,469 discloses triglycerides of the formula.

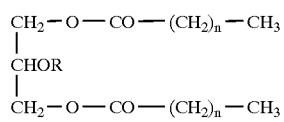

wherein R represents an acyl fragment of a polyunsaturated fatty acid containing 18 to 22 carbon atoms, the acyl fragment being capable of being oxidized, however, R cannot represent the acyl fragment of eicosatetrayn-5, 8, 11, 14-oic acid, and wherein n represents an integer varying from 2 to 16; a process for their preparation, their dietetic and therapeutic applications and compositions containing them.

None of these references either suggest or disclose a structured lipid of the formula:

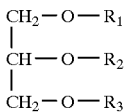

wherein (1) at least one of $R_1, R_2$ or $R_3$ is a fatty acid residue esterified to glycerol and selected from the group consisting of gamma-linolenic acid, dihomogamma-linolenic acid, and active derivatives thereof;

(2) a second of $R_1$, $R_2$ or $R_3$ is a fatty acid residue esterified to glycerol and selected from the group consisting of $C_{18}$–$C_{22}$ n-3 fatty acids and $C_6$–$C_{12}$ fatty acids and active derivatives thereof; and (3) a third of $R_1, R_2$ or $R_3$ is a fatty acid residue esterified to glycerol and selected from the group consisting of $C_6$–$C_{12}$ fatty acids and active derivatives thereof.

Further, these references fail to suggest or disclose a method of modulating metabolic response to trauma and disease states in patients through administering the structured lipid of this invention.

One benefit of this invention over the prior art is that a structured lipid containing a GLA or DHGLA residue and a medium chain fatty acid residue ($C_6$–$C_{12}$) will increase the incorporation of the GLA or DHGLA into tissues and thereby beneficially modify eicosanoid biosynthesis. Medium chain fatty acids in the structured lipid also provide additional fat calories and increase the absorption and clearance of the structured lipid so that the reticuloendothelial system is not blocked with an overabundance of long chain triglycerides. More importantly, medium chain fatty acids do not act as substrates for eicosanoid synthesis. Accordingly, one aspect of the present invention is concerned with a structured lipid which modifies eicosanoid synthesis in a positive manner to produce more series "1" eicosanoids. Another aspect of the invention relates to a physical blend of structured lipids. The first structured lipid contains gamma-linolenic acid and/or dihomogamma-linolenic acid and $C_6$–$C_{12}$ fatty acid residues and a second structured lipid which contains n-3 fatty acid residues and $C_6$–$C_{12}$ fatty acid residues.

An additional aspect of the invention is to provide a method of treating disease and stress states using the specific structured lipid of the invention. These and other features of the invention will be apparent from the following description and the claims.

DISCLOSURE OF THE INVENTION

The present invention features a new family of structured lipids to be used in enteral and parenteral nutritionals, and a method of modulating the metabolic response to trauma and disease using the structured lipids of the invention. The structured lipids of the invention provide particular benefits for modification of the prostanoid synthesis pathway.

There is disclosed a structured lipid having the structural formula:

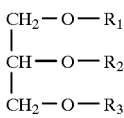

wherein:

1) at least one of $R_1, R_2$ or $R_3$ is a fatty acid residue which is esterified to glycerol and selected from the group consisting of gamma-linolenic acid, dihomogamma-linolenic acid and active derivatives thereof;

2) a second of $R_1, R_2$ or $R_3$ is a fatty acid residue which is esterified to glycerol and selected from the group consisting of $C_{18}$–$C_{22}$ n-3 fatty acids, $C_6$–$C_{12}$ fatty acids and active derivatives thereof; and 3) the third of $R_1, R_2$ or $R_3$ is a fatty acid residue which is esterified to glycerol and is selected from the group consisting of $C_6$–$C_{12}$ fatty acids and active derivatives thereof.

The term "active derivatives", as used herein includes esters, ethers, amines, amides, substituted fatty acids (e.g., halogen substituted fatty acids), and other substitutions which do not affect the beneficial properties of the structured lipid. The structured lipid of this invention must contain either a gamma-linolenic acid or dihomogamma-linolenic acid residue, a $C_{18}$–$C_{22}$ n-3 fatty acid residue and a $C_6$–$C_{12}$ residue. In an alternative embodiment a physical mixture of two structured lipids is disclosed wherein the first structured lipid contains a GLA and/or DHGLA fatty acid residue and a medium-chain fatty acid residue and the second structured lipid contains medium-chain fatty acid residues and n-3 fatty acid residues.

A preferred structured lipid of the invention has a medium chain ($C_6$–$C_{12}$) fatty acid residue in the 2 position, a gamma-linolenic acid or DHGLA residue at 1 or 3 and a 20:5n-3 at 1 or 3.

The $C_{18}$–$C_{22}$ n-3 fatty acids useful in this invention are: alpha-linolenic (18:3n-3), stearidonic (18:4n-3), eicosapentaenoic (20:5n-3) and docosahexanoic (22:6n-3). The $C_6$–$C_{12}$ fatty acids useful in this invention are caproic, caprylic, capric, and lauric.

The invention also features an enteral or parenteral preparation containing specific structured lipids that are prepared from a physical blend of oils. This oil blend is 10–90% by weight an oil which is 5–70% by weight $C_{18}$–$C_{22}$ n-3 fatty acids, and 10–90% of a second oil having 5–70% of fatty acids selected from gamma-linolenic acid and/or dihomogamma-linolenic acid and 10–90% of a third oil which is at least 50% by weight medium chain ($C_6$–$C_{12}$) fatty acid residues. This mixture may then be subjected to a transesterification reaction to yield a reaction product that contains the structured lipids of this invention.

The invention further features an enteral or parenteral nutrition which contains at least two structured lipids of this invention. This combination of structured lipids consists of a first structured lipid containing gamma-linolenic and/or dihomogamma-linolenic acid residues and $C_6$–$C_{12}$ fatty acid residues, and active derivatives thereof; the second structured lipid consists of $C_{18}$–$C_{22}$ n-3 fatty acid residues and $C_6$–$C_{12}$ fatty acid residues and active derivatives thereof.

Another aspect of the invention is a method of modulating the metabolic response to trauma and disease states in patients by administering a dietary supplement or a complete nutritional containing a structured lipid of the invention. This method is particularly pertinent where the trauma and disease states are caused by burns, immune disorders, cardiogenic shock, sepsis, endotoxemia, bacteremia, cancer, chronic obstructive pulmonary diseases, pediatric and adult respiratory distress syndrome, severe inflammatory diseases such as ulcerative colitis, regional enteritis, pancreatitis and atherosclerosis. The dietary supplement or complete nutritional of the invention modulates or reduces the level of series "2" prostanoids and may be administered either enterally or parenterally. If administered parenterally, it is preferably administered as part of a total parenteral diet.

These aspects of the invention will be more fully elucidated in the following detailed description of the invention.

DETAILED DESCRIPTION OF THE INVENTION

The structured lipids of the present invention provide substantial benefits in terms of modifying the prostanoid synthesis pathway, resulting in an improved response to endotoxic shock and other stress states. These dietary supplements will have particular advantageous results when used enterally.

The invention is used in enteral or parenteral nutrition where 5–75% of the calories included in the total diet are taken as fat or lipid. If the nutrition is administered parenterally, the diet is 1–40% by weight as an emulsion of the lipids according to the invention, most preferably at 5–30% by weight. When taken enterally, the lipids according to the invention may be mixed into a complete or incomplete food which supplies other essential nutrients and fats or it may be in the form of a 200–1500 mg capsule.

The use of a structured lipid having both gamma-linolenic acid (or dihomogamma-linolenic acid) and a long-chain polyunsaturated n-3 fatty acid will provide particular benefits to the stressed or otherwise compromised patient. By providing these fatty acids on the same structured lipid, they are presented to the tissue simultaneously. The long-chain polyunsaturated n-3 fatty acid will serve to minimize the elongation of gamma-linolenic acid to arachidonic acid, yielding a better dihomogamma-linolenic acid/arachidonic acid ratio and a shift away from series "2" prostanoid synthesis toward series 1. Since the series "2" prostanoids are pro-inflammatory while the series "1" prostanoids appear to have some beneficial effects in treating inflammation, this will improve the response to endotoxin challenge. Further, the inclusion of the n-3 fatty acids, particularly eicosapentaenoic acid, decreases the oxygenation of arachidonic acid, by competing for binding sites on cyclooxygenase to yield some series "3" prostanoids. As shown in the '618 Patent, the shift from series "2" to series "3" prostanoids also has beneficial effects in treating infection.

The inclusion of $C_6$–$C_{12}$ fatty acid residues in the structured lipid will also have additional benefits. The $C_6$–$C_{12}$ fatty acid residues improve intestinal absorption and direct the structured lipid through the lymphatic rather than the portal pathway, leading to more effective absorption into the systemic circulation. Since higher levels of structured lipid can be absorbed than the physical mixture, (See Jensen et al., previously cited), the structured lipid is a more effective means of delivering the gamma-linolenic acid or dihomogamma-linolenic acid and n-3 fatty acids to the desired location.

Oils rich in gamma-linolenic acid include evening primrose oil which is about 9% GLA by weight, borage oil which is about 25% and black currant seed oil which has about 15%. Other sources of GLA and DHGLA useful in the preparation of the structured lipids of this invention include algae and fungal oils. Oils rich in n-3 fatty acids include most fish oils, in particular menhaden oil which is approximately 22% by weight and certain fruit and vegetable oil such as canola oil which is approximately 10% by weight. Medium chain triglycerides are available primarily by the fractionation of palm kernel oils or coconut oils.

The structured lipid of the invention may be made by any procedure commonly used to make structured lipids generally. For example, an interesterification or transesterification reaction made by mixing oils, or selective fractions of the oils, in stoichiometric proportions and then causing the transesterfication reaction to proceed using catalysts or enzymes could be used. In the alternative, certain companies have discussed the possibility of making specific "designer oils". These companies include Novo-Nordisk Industries A/S which claims to have an enzymatic procedure to direct the synthesis of specific structured lipids. Other companies use different modifications of standard procedures. However, although a standard transesterfication procedure may result in a mixture of the structured lipids of the invention plus other oils, this mixture is intended to be included within the claims, so long as efficacious amounts of the structured lipids of the invention are present.

The following examples using high fat enteral diets still further elucidate the advantages of the invention.

BEST MODE FOR CARRYING OUT THE INVENTION

EXAMPLE I

In this example, the substitution of the n-3 fatty acid eicosapentaenoic acid (EPA; 20:5n-3) or a combination of EPA and gamma-linolenic acid (GLA 18:3n6) for linoleic acid (LA; 18:2n-6) in a diet was investigated. Three groups of pigs were fed isocaloric and isonitrogenous diets for eight days. The diets contained 55% of the calories from either corn oil (an oil containing a large percentage of LA) which was Diet A; fish oil (an oil containing a large percentage of EPA) which was Diet B; or a combination of fish oil and borage oil (a diet containing the blend of EPA and GLA) which was Diet C. All feeding was enteral.

At the end of the eight day feeding period, acute lung injury was induced with intravenous *E. coli* endotoxin. Cardiopulmonary parameters, specifically systemic and pulmonary arterial pressures and arterial blood gases, and cardiac output, were measured and compared.

All of the pigs showed a fall in $PaO_2$ but the EPA and EPA/GLA diets provide substantially equal attenuation in the fall. Similarly, both the EPA and EPA plus GLA diets were better than the LA diet in terms of attenuating the early rise in pulmonary vascular resistance following endotoxin challenge. Following endotoxin infusion, pulmonary vascular resistance (PVR) increased markedly at 20 minutes (Early Phase Response) in the group of pigs fed diet A. At one hour PVR had decreased but remained higher than that observed at 0-time. PVR steadily increased over the next 2 hours and appeared to stabilize between the third and fourth hour (Late Phase Response). The pigs fed diet B did not demonstrate the Early Phase Response to endotoxin infusion, but the Late Phase Response was substantially identical to that observed in the group fed diet B. Feeding pigs diet C also abolished the Early Phase Response to endotoxin infusion, but appeared to attenuate the late phase response. However, the cardiac output of the pigs which had EPA plus GLA was much closer to the baseline levels than either the EPA diet or the LA diet. Accordingly, it is clear that the combination of EPA and GLA provides improvement in treating endotoxic shock and the associated catabolic stress state.

EXAMPLE II

The pathogenesis of adult respiratory distress syndrome is multifactorial and because of the complicated disease process it has been difficult to model in animals. In man, the injury often becomes present with several insults, such as shock and secondary infection, whereas usually only a single insult is tested in animal models. Because of the association between burn injury and sepsis, an animal model has been developed that is clinically relevant to adult respiratory distress syndrome. In the animal model of burn and endotoxin injury, rats are anesthetized and then burned with boiling water on their dorsum to produce a 30% body surface area full-thickness skin lesion. This causes a short-term shocklike syndrome characterized by transient hypotension which is treated with fluid resuscitation. Following resuscitation, there is an increase in energy expenditure and a negative nitrogen balance due to protein wasting for many days. Three days after creating the burn injury and during the hypermetabolic phase, a 10 mg/kg dose of endotoxin was injected intravenously to mimic the clinical development of sepsis in burned patients.

Twenty male Long-Evans rats (250 g) are randomly divided into two treatment groups of equal number. The jugular vein is cannulated (0.025" I.D.×0.047" O.D.) for blood sampling and infusions. An intragastric catheter is surgically implanted into the stomach and passed into the duodenum for enteral feeding. Catheters are exteriorized at the mid-scapular region, tunneled through a protective spring and attached to an infusion swivel that allows for free movement by the rat. While under anesthesia, a 30% (body surface area) third-degree burn injury is produced by immersing the shaven dorsal surface through a preformed mold in a 90–95° C. waterbath for 15 seconds. The rats are fluid resuscitated with an intraperitoneal injection of sterile lactated Ringers (2.5 ml/100 g body wt) and a 4 hour intravenous infusion of 0.9% saline (2.5 ml/hr). This resuscitation procedure ensures 100% survival of burned rats. The rats are housed individually in metabolic cages and allowed water ad libitum.

After burn trauma, the rats are enterally fed for 72 hours. Group I (n=10) receives an intragastric infusion of a corn oil based diet (see Tables 1 and 2; Diet A) and group II (n=10) receives a structured lipid diet (see Tables 1 and 2; Diet B) for 72 hours after the burn injury. Following this 72 hour period, the rats are anesthetized with pentobarbital (30 mg/kg) and the femoral artery is cannulated and a baseline blood sample (0.5 mL) is taken for blood gas and hematology determinations. Tissue blood flow is determined by radiolabelled microspheres and arterial blood pressure is monitored. Blood samples are drawn for analysis of eicosanoids ($PGE_2$, $PGI_2$, 6-keto-$PGF_1$ alpha, $TXB_2$ and $LTB_4$) and platelet aggregation studies.

TABLE 1

COMPOSITION OF THE OIL BLEND FOR THE EXPERIMENTAL DIETS

| | WEIGHT % | |
|---|---|---|
| OIL | DIET A | DIET B |
| Corn | 100 | 0 |
| MCT | 0 | 60 |
| Concentrated fish | 0 | 20 |
| Borage | 0 | 20 |

TABLE 2

FATTY ACID PROFILES FOR THE EXPERIMENTAL DIETS

| | % OF TOTAL BY WEIGHT | |
|---|---|---|
| FATTY ACID | DIET A | DIET B |
| Caprylic (8:0) | 0.0 | 38.4 |
| Capric (10:0) | 0.0 | 21.3 |
| Palmitic (16:0) | 10.9 | 4.4 |
| Oleic acid (18:1n9) | 25.2 | 4.5 |
| Linoleic acid (18:2n6) | 59.4 | 7.5 |
| Gamma-linolenic acid (18:3n6) | 0.0 | 4.6 |

TABLE 2-continued

FATTY ACID PROFILES FOR THE EXPERIMENTAL DIETS

| | % OF TOTAL BY WEIGHT | |
|---|---|---|
| FATTY ACID | DIET A | DIET B |
| Alpha-linolenic acid (18:3n3) | 1.4 | 0.20 |
| Eicosapentaenoic acid (20:5n3) | 0.0 | 5.0 |
| Docosahexaenoic acid (22:6n3) | 0.0 | 2.5 |
| Others* | 3.1 | 11.6 |
| n-6/n-3 ratio | 43.2 | 1.4 |

*Fatty acids less than 1.8% of total fatty acids.

Lung microvascular permeability and radioactive lung-:heart ratios are determined by the localization rate of $^{99m}$-Human Serum Albumin (HSA) in the lungs by gamma-scintigraphy. An intravenous injection of 0.2 mL $^{99m}$-TC-HSA (500–600 μCi) is given to each rat and 20 minutes later a scintigraphic recording is taken using a computerized gamma scintillation camera to determine baseline lung microvascular permeability. Fifteen minutes later the rats are given an intravenous injection of 10 mg/kg *Salmonella enteritidis* endotoxin to model the development of sepsis in burned patients. Four hours after endotoxin injection a second injection of 0.2 mL $^{99}$TC-HSA (500–600 μCi) is given and scintigraphic recordings are taken for 1 hour. Finally, a 0.4 mL intravenous injection of $^{99}$TC-macroaggregrated albumin (500–900 μCi) is used to highlight the left and right lungs by gamma scintigraphy.

Bronchoalveolar lavage cellular analysis is a valuable technique for assessing the inflammatory and immune effector cells present in the lungs of patients. The total and differential cell counts are used in the assessment of the inflammatory response and for predicting disease activity and response to therapy. Bronchoalveolar lavage is performed in anesthetized rats after cannulation of the trachea with tubing attached to a 12 mL syringe containing saline. The abdominal cavity is opened by midline laparotomy and a terminal blood sample (4 mL) is taken from the abdominal aorta. Arterial blood $PCO_2$, $PO_2$, and pH is determined using a blood gas analyzer. A total leukocyte (WBC), differential and platelet count is performed on the blood samples. The total WBC and platelet count is performed on a hemacytometer. Bronchoalveolar lavage fluid is analyzed for eicosanoids and differential cell counts. Total protein content of bronchoalveolar lavage fluid is measured by a modified Lowry technique.

Results from this study will provide convincing evidence on the physiological and clinical effect of the structured lipids disclosed in this invention. Parenteral or enteral administration of structured lipid of this invention will improve survival rate and reduce arterial hypoxemia, pulmonary edema, and systemic hypotension in endotoxin-challenged burned rats. Nutritional support with structured lipids of this invention decreases neutrophil infiltration and accumulation in the lung and protects against endotoxin-induced interstitial edema and lung weight gain and reduces the pulmonary vascular permeability and rate of albumin leak thus protecting against acute lung injury. The experimental evidence will also demonstrate that the structured lipids of the present invention will reduce neutrophil activation since there is a decrease in lung myeloperoxidase content after a septic challenge. This will protect against the development of acute lung injury since activated neutrophils release myeloperoxidase which will interact with superoxide derivatives to form hypochlorous acid and free chlorine and produce severe damage to the vascular endothelium, mitochondria and collagen. Enteral or parenteral nutrition with structured lipids of this invention will decrease blood levels of $PGE_2$, a detrimental pro-inflammatory series "2" prostaglandin, and increase $PGI_1$, a beneficial antiinflammatory series "1" prostaglandin.

Structured lipids according to the invention decrease the level of thromboxane $A_2$, increase the level of prostacyclin, decrease platelet aggregation, improve tissue blood flow and hemodynamics which offers protection against endotoxic and septic shock. Structured lipids of the invention will reduce neutrophil accumulation in lung and $LTB_4$ levels in bronchoalveolar fluid obtained during the early stages of endotoxin-induced acute lung inflammation. $LTB_4$ is a metabolite of arachidonic acid that has potent chemotactic activity for neutrophils and is responsible for the recruitment and accumulation of neutrophils in the lung. The decrease in $LTB_4$ is closely related to decreases in neutrophil recruitment in the lungs of endotoxin-challenged burned rats. Structured lipids of the invention will increase the incorporation of n-3 fatty acids and decrease the ratio of n-6 to n-3 fatty acids in membrane phospholipids of alveolar and peritoneal macrophages and lung and liver. In vitro studies of the effects of endotoxin on alveolar macrophages showed that structured lipids of the invention reduce the biosynthesis of harmful series-"2" prostaglandins and leukotrienes ($LTB_4$).

INDUSTRIAL APPLICABILITY

The foregoing examples are merely illustrative and are not intended to be limiting to the scope of the invention. The medical community has long sought a nutritional product or supplement that favors an anti-inflammatory, vasodilatory state with less platelet aggregation. The novel lipids of this invention meet these goals by placing on the glycerol backbone residues of GLA or DHGLA, MCT and n-3 fatty acids. The invention is described by the following claims.

We claim:

1. A structured lipid having the formula:

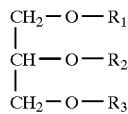

in which $R_1$, $R_2$ and $R_3$ are fatty acid residues esterified to a glycerol backbone, and wherein
   (a) a first one of fatty acid residues $R_1$, $R_2$ and $R_3$ is selected from the group consisting of gamma-linolenic acid, dihomogamma-linolenic acid and active derivatives thereof;
   (b) a second one of fatty acid residues $R_1$, $R_2$ and $R_3$ is selected from the group consisting of $C_{18}$–$C_{22}$ n-3 fatty acids and active derivatives thereof; and
   (c) a third one of fatty acid residues $R_1$, $R_2$ and $R_3$ is selected from the group consisting of $C_6$–$C_{12}$ fatty acids and active derivatives thereof.

2. The structured lipid of claim 1 wherein the fatty acid residue $R_2$ consists of gamma-linolenic acid, dihomogamma-linolenic acid or active derivatives thereof.

3. The structured lipid of claim 1 wherein the fatty acid residue $R_2$ consists of consisting of $C_{18}$–$C_{22}$ n-3 fatty acids or active derivatives thereof.

4. The structured lipid of claim 1 wherein the fatty acid residue $R_2$ consists of $C_6$–$C_{12}$ fatty acids or active derivatives thereof.

5. A structured lipid according to claim 1 in which:
   a) $R_1$ is gamma-linolenic acid;
   b) $R_2$ is caprylic acid, and;
   c) $R_3$ is eicosapentaenoic acid.

6. The structured lipid of claim 1 wherein said $C_{18}$–$C_{22}$ n-3 fatty acid is selected from the group consisting of alpha-linolenic, stearidonic, eicosapentaenoic and docosahexaenoic.

7. The structured lipid according to claim 1 in which said n-3 fatty acid is alpha-linolenic.

8. The structured lipid according to claim 1 in which said n-3 fatty acid is stearidonic.

9. The structured lipid according to claim 1 in which said n-3 fatty acid is eicosapentaenoic.

10. The structured lipid according to claim 1 in which said n-3 fatty acid is docosahexaenoic.

11. The structured lipid according to claim 1 in which said first one of said fatty acid residue $R_1$, $R_2$, and $R_3$ is gamma-linolenic acid.

12. The structured lipid according to claim 1 in which said first one of said fatty acid residue $R_1$, $R_2$, and $R_3$ is dihomogamma-linolenic acid.

13. The structured lipid according to claim 1 in which said $C_6$–$C_{12}$ fatty acid is selected from the group consisting of caproic, caprylic, capric, and lauric.

14. The structured lipid according to claim 1 in which said $C_6$–$C_{12}$ fatty acid is caproic.

15. The structured lipid according to claim 1 in which said $C_6$–$C_{12}$ fatty acid is caprylic.

16. The structured lipid according to claim 1 in which said $C_6$–$C_{12}$ fatty acid is capric.

17. The structured lipid according to claim 1 in which said $C_6$–$C_{12}$ fatty acid is lauric.

18. The structured lipid according to claim 1 in which:
   a) $R_1$ is eicosapentaenoic acid;
   b) $R_2$ is a $C_6$–$C_{12}$ fatty acid, and;
   c) $R_3$ is gamma-linolenic acid.

19. The structured lipid according to claim 1 in which:
   a) said first one of said fatty acid residues $R_1$, $R_2$, and $R_3$ is gamma-linolenic acid;
   b) said second one of said fatty acid residues $R_1$, $R_2$, and $R_3$ is eicosapentaenoic acid, and;
   c) said third one of said fatty acid residues $R_1$, $R_2$, and $R_3$ is a $C_6$–$C_{12}$ fatty acid.

20. The structured lipid of claim 19 wherein one fatty acid residue is a gamma-linolenic-acid or dihomogamma-linolenic acid residue, the second fatty acid residue is a $C_6$–$C_{12}$ fatty acid residue, and the third fatty acid residue is a $C_{18}$–$C_{22}$ n-3 fatty acid residue.

* * * * *